United States Patent [19]

Creed

[11] Patent Number: 4,863,380
[45] Date of Patent: Sep. 5, 1989

[54] GUM TREATING METHOD AND DEVICE

[76] Inventor: Jill A. Creed, 3955 W. Vickery, Fort Worth, Tex. 76107

[21] Appl. No.: 89,236

[22] Filed: Aug. 25, 1987

[51] Int. Cl.$^4$ .......................... A61C 15/00; A61H 7/00
[52] U.S. Cl. .................... 433/89; 128/62 A; 128/65; 128/67; 132/322
[58] Field of Search ............... 433/89; 128/62 A, 65, 128/67; 132/89, 93; 222/211

[56] References Cited

U.S. PATENT DOCUMENTS

| | | | |
|---|---|---|---|
| 719,017 | 1/1903 | Lenhardsson | 132/89 |
| 2,303,667 | 12/1942 | Taborski | 132/89 X |
| 2,684,063 | 7/1954 | Bileth | 128/62 A |
| 2,888,696 | 6/1959 | Longert | 15/136 |
| 2,976,560 | 3/1961 | Turner | 15/569 |
| 3,070,089 | 12/1962 | Dick | 137/855 X |
| 3,359,588 | 12/1967 | Kobles | 128/52 A X |
| 3,391,696 | 7/1968 | Woodward | 433/89 |
| 3,675,645 | 7/1972 | Samiran et al. | 128/62 A |
| 3,677,264 | 7/1297 | Brockman | 128/62 A |
| 3,963,150 | 6/1976 | Steiman et al. | 222/211 |
| 4,087,024 | 5/1978 | Martin et al. | 222/211 |
| 4,429,434 | 2/1984 | Sung-Shan | 15/341 |

Primary Examiner—Martin P. Schwadron
Assistant Examiner—Allen J. Flanigan
Attorney, Agent, or Firm—James E. Bradley

[57] ABSTRACT

A device for treating gums allows a treating solution to be injected into contact with the gums between the teeth. The device is a hand held unit having a reservoir and a tubular neck joined to it. A hollow rubber tip is secured to the upper end of the neck. The tip has a number of ports in its sidewall. The device has a check valve in it that prevents fluid in the mouth from entering into the neck. Squeezing the reservoir expels fluid through the tip into contact with the gums between the teeth. The tip is small enough to be inserted partially between the teeth into contact with the gums.

3 Claims, 1 Drawing Sheet

4,863,380

GUM TREATING METHOD AND DEVICE

BACKGROUND OF THE INVENTION

1. Field of the Invention

This invention relates in general to devices for cleaning teeth, and in particular to a device for massaging and treating the gums between the teeth.

2. Description of the Prior Art

The formation of plaque or calculus on the teeth can lead to serious problems. If not checked, plaque may cause inflammation of the gum tissues and swelling. This creates pockets of tissue above the bone. Dental calculus can form on the tooth in these pockets below the level of the tissue. Also, exudates form in the sulcular fluids, which create an oxygen free environment. Bacteria thrive on the absence of oxygen in the pockets. Bone loss may occur, and ultimately, if not checked, the tooth will lose its support and be lost.

Gum tissue of this type is normally treated by regular trips to a dentist's office where dental hygenists will remove the dental calculus around the teeth. If the pockets that are formed in the gums are sufficiently deep, a periodontist may reduce the depth of the pockets and level off the bone loss through surgery. Still, if the person is unable to keep the area between the teeth clean, inflammation will occur again.

Gum stimulators having solid rubber tips are available to massage the gum and clean between the teeth. Dental flossing is used. Also, a device which sprays a jet of water using an electrical pump is used.

SUMMARY OF THE INVENTION

A device is used to clean between the teeth and also supply an oxygenating liquid to the pockets in the gum tissues to kill harmful anaerobic bacteria and inhibit plaque buildup. This process begins a natural resolution of the gum disease cycle. This device has a reservoir which is filled with the treating solution, preferably an oxygenating solution. A neck leads up from the reservoir to a rubber tip. The rubber tip has holes in its sidewall for discharging the liquid out between the teeth into the pockets and around the gums.

The treating liquid is expelled from the reservoir by squeezing the reservoir. To prevent fluid in the mouth from reentering the neck when squeezing pressure is removed, a check valve is used. Preferably, a handle extends down from the reservoir. The optional handle is small enough to fit inside a conventional toothbrush holder.

DESCRIPTION OF THE PREFERRED EMBODIMENT

Figures 1, 2:
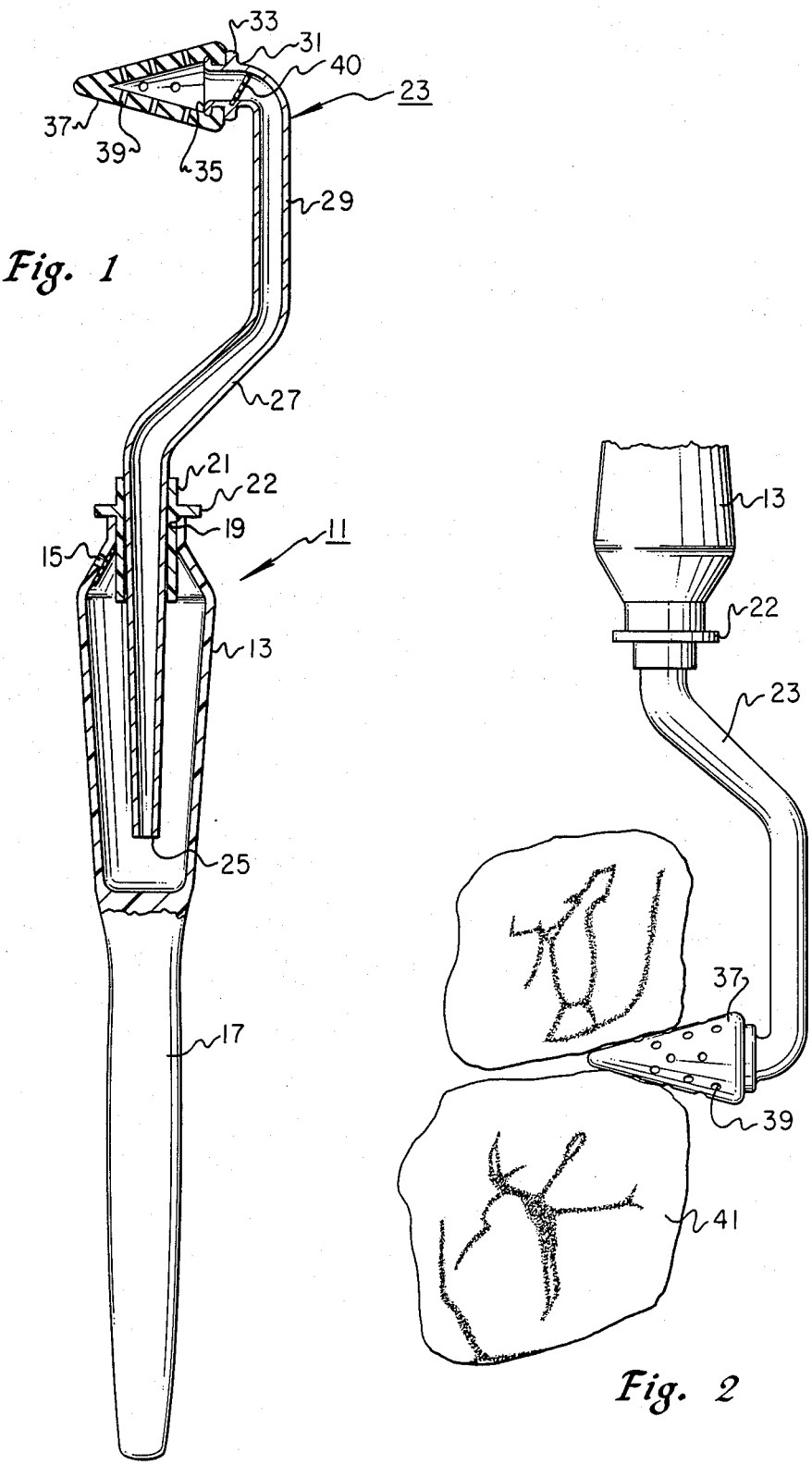
FIG. 1 is a partial vertical section view of a device constructed in accordance with this invention.
FIG. 2 is a partial side view of the device in FIG. 1, shown inserted between two teeth.

Referring to FIG. 1, device 11 is a small hand held instrument not much larger than a conventional toothbrush. It has a flexible, resilient reservoir 13 of an elastomeric rubber-like material. Reservoir 13 is shown in its natural state, which may be considered the expanded state. The user may squeeze the sidewalls of the reservoir 13, causing it to contract to a contracted state of much lesser volume. When released, the resiliency of the sidewalls of reservoir 13 will bring back to its natural state shown in FIG. 1.

A check valve 15 is located in a hole that extends through the sidewall of reservoir 13 near the top. Check valve 15 allows air to flow into the reservoir 13 when it is expanded back to its natural state. Check valve 15 prevents air or fluid from passing through it out of the reservoir 13 when the reservoir 13 is squeezed. Check valve 15 may be of various types, and is shown as a simple flexible flap.

A solid handle 17 is integrally joined to the reservoir 13 and extends downward. Handle 17 is about twice the length of the reservoir 13. The cross-sectional dimension of handle 17 is sufficiently small so that it will fit into a conventional toothbrush holder.

An opening 19 is located at the upper end of reservoir 13. An adapter 21 fits tightly into the opening 19. Adapter 21 is a tubular member having an external flange 22 that bears against the rim surrounding opening 19 of the reservoir 13.

A tubular neck 23 extends through the adapter 21. The neck 23 is tightly received in the adapter 21. Adapter 21 frictionally retains the neck 23 in the reservoir 13 by means of the tight fit between the opening 19 of the reservoir 13 and the adapter 21. Adapter 21 also provides a seal to prevent liquid in the reservoir 13 from leaking between the opening 19 and adapter 21, and between the neck 23 and adapter 21.

Neck 23 is a rigid plastic member. The neck 23 extends down into the reservoir 13. The lower end 25 of neck 23 is located close to the bottom of the reservoir 13. The lower portion of neck 23 is coaxial with the longitudinal axis of the reservoir 13. An intermediate portion 27 extends upward from the lower portion at an angle of about 45 degrees relative to the longitudinal axis of reservoir 13. An upper portion 29 joins the intermediate portion 27. The upper portion 29 has an axis that is parallel to but offset from the longitudinal axis of reservoir 13.

An upper end 31 is located on the upper portion 29 of neck 23. Upper end 31 faces 90 degrees laterally from the axis of the upper portion 29 and also from the axis of the reservoir 13. The upper end 31 has an external flange 33 near its end. A lip 35 is formed on the edge of the upper end 31 and spaced from the flange 33. This results in a channel between the lip 35 and the flange 33.

A flexible elastomeric or rubber tip 37 is releasably inserted on the upper end 31. The tip 37 is conical and hollow with an axis that coincides with the axis of the upper end 31. Tip 37 has a base that fits tightly in the channel between the lip 35 and flange 33. Tip 37 has a plurality of ports 39 in its sidewall. Ports 39 extend laterally outward from the axis of the tip 37. Ports 39 are inclined relative to the axis of the tip 37 to direct fluid generally radially outward from the axis of the tip 37. There are no ports 35 located on the apex of the tip 37. Consequently, no liquid will flow out along the axis of the tip 37. As shown in FIG. 2, at least the forward portion or apex of the tip 37 is small enough so that it will locate between at least two of the user's teeth 41.

A check valve 40 is located in the upper end 31 of neck 23. Check valve 40 allows fluid to flow out from neck 23, but prevents any flow in the reverse direction back into the tip 37. Check valve 40, similar to check valve 15, is a flexible elastomeric flap.

In operation, the user pulls the neck 23 and adapter 21 from the opening 19 of reservoir 13. The user then fills the reservoir 13 with a treating liquid. Preferably, this is a solution that provides oxygen to the pockets in the gums surrounding the teeth. A typical oxygenating solution is dilute hydrogen peroxide. Then, the user inserts the adapter 21 and neck 23 back into the reservoir 13.

He places the tip 37 between the teeth 41, massaging the gums by moving the tip 37 back and forth. This displaces present sulcular fluids, which are then replaced with an oxygenating solution. The user squeezes repeatingly on the reservoir 13. This expels bursts of the treating liquid into the spaces between the teeth 41 and down into the pockets surrounding the teeth 41. The user moves from tooth to tooth on the inside and outside until complete.

Check valve 15 prevents any fluid from flowing out the check valve 15 when the reservoir 13 is squeezed. Check valve 15 allows air to be drawn into the reservoir 13 when squeezing pressure is released, to allow the reservoir 13 to return to its normal shape. The check valve 40 prevents any suction created by the return of reservoir 13 to its normal state from drawing any fluid back into the neck 23. This avoids contaminating or diluting any remaining fluid in the reservoir 13 with fluid from the mouth. The check valve 15 also reduces suction at the tip 37 by admitting air to the reservoir 13 when it returns to its natural state. If the reservoir 13 still contains fluid after the user has treated the gums, he may retain it in the reservoir 13 for use on a following day.

The invention has significant advantages. The device provides oxygenating solution to areas in the gums that otherwise would not receive such treatment merely by using the solution as a mouthwash. The device massages the gums, increasing the blood flow. The treatment disrupts the formation of plaque by adding oxygen to an area otherwise free of oxygen. This in turn results in a reduction of pocket depth and reduction in the need for conventional dental surgery.

While the invention has been shown in only one of its forms, it should be apparent to those skilled in the art that it is not so limited, but is susceptible to various changes without departing from the scope of the invention.

I claim:

1. A device for treating gums, comprising:
a flexible reservoir containing a treating liquid and having a longitudinal axis, the reservoir having an open upper end and being movable from an expanded position to a contracted position by squeezing the reservoir;
a tubular neck extending from the reservoir, the neck having a lower portion extending into the open upper end and coaxial with the longitudinal axis of the reservoir, an intermediate portion extending upward and laterally from the lower portion in a first direction, and an upper portion extending upward from the intermediate portion offset from the longitudinal axis, the upper portion having an upper end pointing in a second direction away from the first direction;
seal means for sealing the lower portion of the neck in the open upper end of the reservoir;
a hollow rubber-like conical tip secured to the upper end of the neck, the tip having an axis that extends laterally relative to the longitudinal axis of the reservoir, and being dimensioned to insert at least partially between at least some of the user's teeth into contact with the gums, the longitudinal axis of the reservoir passing through the tip;
a plurality of ports extending through the tip at an inclination relative to the axis of the tip, so that the reservoir when squeezed to the contracted position, forces the treating liquid through the ports into contact with the gums; and
an elongated handle end extending downward from the reservoir a distance greater than the length of the reservoir, for insertion into a toothbrush holder.

2. A device for treating gums, comprising:
a flexible reservoir containing a treating liquid and having a longitudinal axis, the reservoir having an open upper end and being movable from an expanded position to a contracted position by squeezing the reservoir;
a tubular neck extending from the reservoir, the neck having a lower portion extending into the open upper end and coaxial with the longitudinal axis of the reservoir, an intermediate portion extending upward and laterally from the lower portion in a first direction, and an upper portion extending upward from the intermediate portion offset from the longitudinal axis, the upper portion having an upper end pointing in a second direction away from the first direction;
seal means for sealing the lower portion of the neck in the open upper end of the reservoir;
a hollow rubber-like conical tip secured to the upper end of the neck, the tip having an axis that extends laterally relative to the longitudinal axis of the reservoir, and being dimensioned to insert at least partially between at least some of the user's teeth into contact with the gums, the longitudinal axis of the reservoir passing through the tip;
a plurality of ports extending through the tip at an inclination relative to the axis of the tip, so that the reservoir when squeezed to the contracted position, forces the treating liquid through the ports into contact with the gums; and
wherein the seal means comprises a sleeve encircling the neck and frictionally engaging the open upper end of the reservoir to allow filling of the reservoir by removing the neck and sleeve from the reservoir and pouring the liquid into the upper end of the reservoir.

3. A device for treating gums, comprising:
a flexible reservoir containing a treating liquid and having a longitudinal axis, the reservoir having an open upper end and being movable from an expanded position to a contracted position by squeezing the reservoir;
a tubular neck extending from the reservoir, the neck having a lower portion extending into the open upper end and coaxial with the longitudinal axis of the reservoir, an intermediate portion extending upward and laterally from the lower portion in a first direction, and an upper portion extending upward from the intermediate portion offset from the longitudinal axis, the upper portion having an upper end pointing in a second direction away from the first direction;
seal means for sealing the lower portion of the neck in the open upper end of the reservoir;
a hollow rubber-like conical tip secured to the upper end of the neck, the tip having an axis that extends laterally relative to the longitudinal axis of the reservoir, and being dimensioned to insert at least partially between at least some of the user's teeth into contact with the gums;

a plurality of ports extending through the tip at an inclination relative to the axis of the tip, so that the reservoir when squeezed to the contracted position, forces the treating liquid through the ports into contact with the gums; and wherein the seal means comprises a sleeve encircling the neck and frictionally engaging the open upper end of the reservoir to allow filling of the reservoir by removing the neck and sleeve from the reservoir and pouring the liquid into the upper end of the reservoir.

* * * * *